(12) United States Patent
Hietbrink et al.

(10) Patent No.: US 10,557,968 B2
(45) Date of Patent: Feb. 11, 2020

(54) MARINE CABLE DEVICE ADAPTED FOR THE PREVENTION OF FOULING

(71) Applicant: KONINKLIJKE PHILIPS N.V., Eindhoven (NL)

(72) Inventors: Roelant Boudewijn Hietbrink, Utrecht (NL); Bart Andre Salters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 92 days.

(21) Appl. No.: 15/536,153

(22) PCT Filed: Dec. 14, 2015

(86) PCT No.: PCT/EP2015/079668
§ 371 (c)(1),
(2) Date: Jun. 15, 2017

(87) PCT Pub. No.: WO2016/096770
PCT Pub. Date: Jun. 23, 2016

(65) Prior Publication Data
US 2017/0336530 A1 Nov. 23, 2017

(30) Foreign Application Priority Data
Dec. 16, 2014 (EP) .................................. 14198291

(51) Int. Cl.
*A61L 2/10* (2006.01)
*G01V 1/38* (2006.01)
(Continued)

(52) U.S. Cl.
CPC ................ *G01V 13/00* (2013.01); *A61L 2/10* (2013.01); *G01V 1/201* (2013.01); *G01V 1/38* (2013.01)

(58) Field of Classification Search
CPC .......... G01V 1/38; G01V 1/201; G01V 13/00; G01V 13/15; G01V 8/24; A61L 2/10
See application file for complete search history.

(56) References Cited

U.S. PATENT DOCUMENTS 6,468,433 B1 * 10/2002 Tribelski ............... A01M 1/226
210/748.06
7,049,622 B1 * 5/2006 Weiss .................... G01F 23/292
250/573

(Continued)

FOREIGN PATENT DOCUMENTS

JP  2012040538 A  3/2012
WO  2012039625 A1  3/2012

(Continued)

*Primary Examiner* — Nicole M Ippolito
*Assistant Examiner* — Sean M Luck

(57) ABSTRACT

The present invention provides a marine cable device configured for preventing or reducing biofouling along its exterior surface, which during use is at least temporarily exposed to water. The marine cable device according to the present invention comprises at least one light source configured to generate an anti-fouling light and at least one optical medium configured to receive at least part of the anti-fouling light. The optical medium comprises at least one emission surface configured to provide at least part of said anti-fouling light on at least part of said exterior surface.

15 Claims, 5 Drawing Sheets

(51) Int. Cl.
*G01V 1/20* (2006.01)
*G01V 13/00* (2006.01)

(56) References Cited

U.S. PATENT DOCUMENTS

| | | | |
|---|---|---|---|
| 7,329,857 B1* | 2/2008 | Weiss | G01F 23/2925 |
| | | | 250/227.11 |
| 2003/0063857 A1* | 4/2003 | Sakamoto | G02B 6/02119 |
| | | | 385/37 |
| 2007/0097108 A1* | 5/2007 | Brewer | G02B 6/06 |
| | | | 345/204 |
| 2008/0192463 A1* | 8/2008 | Fan | F21K 9/00 |
| | | | 362/219 |
| 2008/0205892 A1* | 8/2008 | Baiden | H04B 13/02 |
| | | | 398/104 |
| 2009/0072165 A1* | 3/2009 | Townsend | F41J 2/02 |
| | | | 250/504 R |
| 2010/0226116 A1* | 9/2010 | Brainard | F21V 13/04 |
| | | | 362/84 |
| 2011/0019403 A1* | 1/2011 | Tsai | F21V 21/002 |
| | | | 362/235 |
| 2011/0197919 A1 | 8/2011 | Tilley | |
| 2014/0247690 A1 | 9/2014 | Macquin et al. | |

FOREIGN PATENT DOCUMENTS

| | | |
|---|---|---|
| WO | 2014135706 A2 | 9/2014 |
| WO | 2014188347 A1 | 11/2014 |

\* cited by examiner

MARINE CABLE DEVICE ADAPTED FOR THE PREVENTION OF FOULING

CROSS-REFERENCE TO PRIOR APPLICATIONS

This application is the U.S. National Phase application under 35 U.S.C. § 371 of International Application No. PCT/EP2015/079668, filed on 14 Dec. 2015, which claims the benefit of European Patent Application No. 14198291.8, filed on 16 Dec. 2014. These applications are hereby incorporated by reference herein.

TECHNICAL FIELD

The present disclosure relates to a marine cable device which is adapted for the prevention of fouling, commonly referred to as anti-fouling. The disclosure specifically relates to anti-fouling of the subsea cables such as umbilicals or seismic streamer cables.

BACKGROUND

Biofouling or biological fouling is the accumulation of microorganisms, plants, algae, and/or animals on surfaces. The variety among biofouling organisms is highly diverse and extends far beyond attachment of barnacles and seaweeds. According to some estimates, over 1800 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents them from settling, organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and heat exchangers suffer from reduced performance. Hence the topic of anti-fouling, i.e. the process of removing or preventing biofouling from forming, is well known. In industrial processes, bio-dispersants can be used to control biofouling. In less controlled environments, organisms are killed or repelled with coatings using biocides, thermal treatments or pulses of energy. Alternatively mechanical structures for removing the fouling already formed on the specific structure are developed.

Several marine cable devices are used in moving and or stationary marine structures. Subsea umbilicals are one of these which are deployed on the seabed (ocean floor) to supply necessary control, energy (electric, hydraulic) and chemicals to subsea oil and gas wells, subsea manifolds and any subsea system requiring remote control, such as a remotely operated vehicle. Subsea intervention umbilicals are also used for offshore drilling or workover activities. The mass of the umbilical changes as fouling starts to grow. This causes an additional load for all mooring elements. This becomes even worse if the vibration frequency of a system synchronizes with the frequency of waves in the water. Accordingly fouling on the outer surface of the umbilical is not desired.

Another area where a marine cable device is often used is marine seismic surveying. Marine seismic surveying is typically performed using cables towed near the surface of a body of water. The marine cable device in this case is often called a "streamer" which is in the most general sense is a marine cable device towed by a seismic vessel. The cable in this embodiment has a plurality of seismic sensors disposed thereon at spaced apart locations along the length of the cable. The seismic sensors are typically hydrophones, but can also be any type of sensor that is responsive to the pressure in the water, or to changes therein with respect to time. A typical marine seismic cable device can be up to several kilometers in length, and can include thousands of individual seismic sensors. The buildup of fouling on the cable can disturb signal transfer fidelity and increase cable drag.

Antifouling arrangements for such marine cable devices are known in the art. US2011197919 and JP2012040538 relate to mechanical antifouling systems for marine cable devices.

SUMMARY OF THE INVENTION

Bio-fouling on the exterior surface of marine cable devices causes severe problems. The main issue is the change in the properties of the cable such as its mass or noise level etc. This causes the cable not being able to provide its function as designed or further physical phenomena that poses a problem for the cable or the whole structure cable is attached to.

There are numerous organisms that contribute to biofouling. This includes very small organisms like bacteria and algae, but also very large ones such as crustaceans. The environment, temperature of the water, and purpose of the system all play a role here. The environment of a box cooler is ideally suited for bio-fouling: the fluid to be cooled heats up to a medium temperature and the constant flow of water brings in nutrients and new organisms.

Accordingly methods and apparatus are necessary for anti-fouling. Prior art systems, however, are inefficient in their use, require regular maintenance and are costly to implement. Hence, it is an aspect of the invention to provide a marine cable device with an alternative anti-fouling system according to the appended independent claim. The dependent claim define advantageous embodiments.

Herewith an approach is presented based on optical methods, in particular using ultra-violet light (UV). It appears that most micro-organisms are killed, rendered inactive or unable to reproduce with 'sufficient' UV light. This effect is mainly governed by the total dose of UV light. A typical dose to kill 90% of a certain micro-organism is 10 mW-hours per square meter.

The marine cable device in accordance with the present invention might supply and/or transport at least one of data, electricity, water, gas or oil to or from the seabed. Alternatively it might also carry along the exterior surface at least one or more sensors, optical and/or electrical equipment. In that sense any and all underwater cable like structures are within the scope of the invention. Such a cable device maybe used in a vessel, a stationary marine structure, an offshore structure or a seismic surveying structure.

The marine cable device in accordance with the present invention is configured for preventing or reducing biofouling along its exterior surface which is during use is at least temporarily exposed to water. The marine cable device comprises at least one optical medium configured to receive at least part of an anti-fouling light generated by at least one light source, the optical medium comprising at least one emission surface configured to provide at least part of said anti-fouling light on at least part of said exterior surface.

In a particular embodiment the marine cable device further comprises the at least one light source configured to generate the anti-fouling light to be received by the optical medium.

In an embodiment, the marine cable device the anti-fouling light emitted by the light source is in the UV or blue wavelength range from about 220 nm to about 420 nm, preferably about 260 nm. Suitable anti-fouling levels are reached by UV or blue light from about 220 nm to about 420 nm, in particular at wavelengths shorter than about 300 nm, e.g. from about 240 nm to about 280 nm which corresponds to what is known as UV-C. Anti-fouling light intensity in the range of 5-10 mW/m$^2$ (milliwatts per square meter) can be used. Alternatively combinations of UV-A and UV-C light can also be used. Obviously higher doses of anti-fouling light would also achieve the same if not better results.

In a version of the above described embodiment where UVA light is used as the anti-fouling light the outside of the optical medium is coated with TiO2 as TiO2 is a physical sunscreen protecting against UVA.

In an embodiment of the marine cable device the light source is a laser, and at least one optical medium is in the form of a transparent fiber fed by the said laser light source. The laser light source is preferably located close to the end of the fiber which is outside the water and arranged so as to provide anti-fouling light from this end. The fiber guides the anti-fouling light through its length and provides the anti-fouling light on the exterior of the cable onto which it is coupled. Accordingly fouling is prevented or reduced on the exterior surface on which anti-fouling light is provided.

In an embodiment of the marine cable device the optical medium is made of quartz and/or glass. Obviously alternative forms of plastics can also be used for the production of the optical medium. The optical medium is preferably extruded from these materials into a semi flexible rod form.

In an embodiment of the marine cable device multiple emission surfaces are arranged on the optical medium. Accordingly the anti-fouling light is out-coupled on the exterior surface of the cable in a uniform manner and hence effective antifouling is achieved throughout a desired length of the cable.

In an embodiment of the marine cable device more than one optical medium in the form of a fiber along at least part of the length of the marine cable device is provided. Such an embodiment is suitable if for example it is necessary to provide redundancy for the anti-fouling light to assure sufficient doses of anti-fouling light is provided on the external surface of the marine cable device. In a version of this embodiment the optical mediums might be provided with different refractive indices and/or wavelengths. Alternatively the light sources providing anti-fouling light to each optical medium can provide light at a different wavelength. Accordingly anti-fouling light of different colors can be provided simultaneously. Alternatively multiple optical mediums can also be used to provide UVA and UVC simultaneously to achieve the desired level of UV doses for optimum antifouling efficiency.

The germicidal doses needed can also easily be achieved with existing low cost, lower power UV LEDs. LEDs can generally be included in relatively smaller packages and consume less power than other types of light sources. LEDs can be manufactured to emit (UV) light of various desired wavelengths and their operating parameters, most notably the output power, can be controlled to a high degree.

Accordingly in another embodiment of the marine cable device an array of light sources in the form of light-emitting diodes are used.

In a version of this embodiment the array of LED light sources are preferably embedded in the optical medium which is a UV transparent silicone composition in the form of a film and the film is then applied on the exterior surface of the cable so as to provide the anti-fouling light on the said exterior. In this embodiment the distance between the LED's should be determined based on the absorption of the UV light and the opening angle.

In an alternative embodiment it is also possible that the optical medium in the form of a fiber is embedded into a further optical medium which is a UV transparent silicone layer. In this embodiment the secondary optical medium in the form of a silicone layer further guides the anti-fouling light from first optical medium in the form of the fiber towards areas of the exterior surface of the cable.

In alternative embodiments of the invention the optical medium into which light sources or further optical mediums are embedded can be a sandwich of different types of materials such as transparent silicon in the middle and tougher but more absorbing silicone layers on the outside. Another possibility is the addition of air enclosures, where small air tubes are included in the layer. Alternatively quartz can also be used instead of air.

In a preferred embodiment of the marine cable device the optical medium is wrapped around the exterior surface of the cable. Accordingly the anti-fouling light is provided on the exterior surface of the cable in a uniform manner as well as ease of installation is achieved.

In a version of the above described embodiment the optical medium is wrapped with a variable pitch along at least part of the length of the marine cable device, arranged such that the pitch angle is smaller in the areas with more fouling risk. For example the pitch angle might decrease as the cable moves deeper in the water as the intensity of the light guided will decrease by distance traveled. Accordingly a uniform distribution of antifouling light can be achieved through-out the length. On the other hand as the optical medium reaches even deeper in water the environmental properties in the sea change in such a way that after a depth less fouling is expected. In this case the pitch angle is then increased after a certain depth to optimize the relation between the fouling level and the anti-fouling light provided on the exterior surface.

In an alternative embodiment the optical medium is arranged lengthwise on the exterior surface of the cable, in straight lines parallel to cable core. Accordingly ease of manufacturing will be achieved where the core, exterior surface and the optical medium would be assembled together before final wrapping is done.

In an embodiment the marine cable device comprises a reflective layer in between the optical medium and the cable so as to decrease the amount of anti-fouling light absorbed by the exterior surface and guide more antifouling light towards possible fouling area.

In an embodiment the marine cable device comprises at least one spacer in between the reflective layer and the exterior surface. Accordingly a small layer of air or water is created to improve the efficiency as both water and air absorb less UVC.

In an embodiment the marine cable device comprises means for harvesting energy to power the light sources. Accordingly the need for external power sources is minimized and the cost efficiency of the system is increased.

In a version of the above embodiment means for harvesting are Peltier elements. In this embodiment the warm fluids that rise from the ocean floor upwards and the corresponding temperature difference is used to harvest energy via the Peltier elements.

In an embodiment of the marine cable device the optical medium is colored or comprises Fluor particles so as to create a yellow glow as it is desired for all subsea structures to have a yellow color primarily due to increased visibility underwater.

In an embodiment of the marine cable device the optical medium could also have small side branches, with some light leaking into them. Accordingly the anti-fouling light is distributed better over the entire area of the external surface of the cable.

The exterior surface of the cable can be covered in sections, having each a separated anti-fouling light source. For example an optical medium in the form of a fiber may go straight down to wanted depth/length of the cable and start spiraling from there. The anti-fouling light source could so remain placed above the waterline.

The term "comprise" includes also embodiments wherein the term "comprises" means "consists of". The term "comprising" may in an embodiment refer to "consisting of" but may in another embodiment also refer to "containing at least the defined species and optionally one or more other species".

It is to be understood that the terms so used are interchangeable under appropriate circumstances and that the embodiments of the invention described herein are capable of operation in other sequences than described or illustrated herein.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The article "a" or "an" preceding an element does not exclude the presence of a plurality of such elements. The mere fact that certain measures are recited in mutually different dependent claims does not indicate that a combination of these measures cannot be used to advantage.

The invention further applies to a device comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

Figure 1:
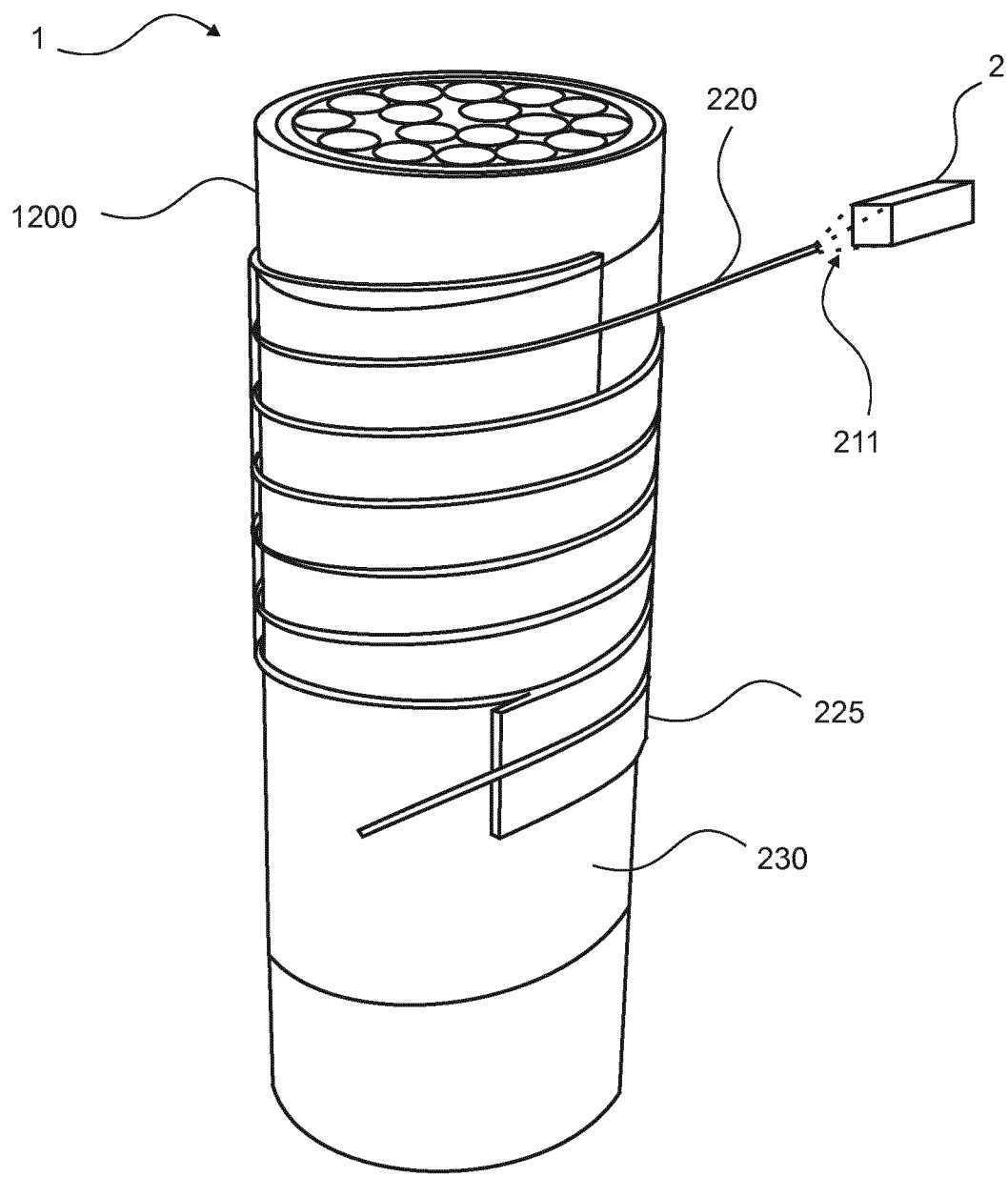
FIG. 1 is a schematic representation of an embodiment of the marine cable device.

The drawings are not necessarily on scale.

DETAILED DESCRIPTION OF THE EMBODIMENTS

While the disclosure has been illustrated and described in detail in the drawings and foregoing description, such illustration and description are to be considered illustrative or exemplary and not restrictive; the disclosure is not limited to the disclosed embodiments. It is further noted that the drawings are schematic, not necessarily to scale and that details that are not required for understanding the present invention may have been omitted. The terms "inner", "outer", "along", "longitudinal", "bottom" and the like relate to the embodiments as oriented in the drawings, unless otherwise specified. Further, elements that are at least substantially identical or that perform an at least substantially identical function are denoted by the same numeral.

FIG. 1 shows as an embodiment, a schematic view of a marine cable device (1) configured for preventing or reducing biofouling along its exterior surface (1200), that during use is at least temporarily exposed to water. In this embodiment the marine cable device (1) further comprises the at least one light source (2) configured to generate an anti-fouling light (211) and at least one optical medium (220) configured to receive at least part of the anti-fouling light (211), the optical medium (220) comprising at least one emission surface configured to provide at least part of said anti-fouling light (211) on at least part of said exterior surface (1200). In this embodiment the light source (2) is a laser and one optical medium (220) is in the form of a UV transparent fiber fed by the said laser light source (2). In this embodiment the optical medium (220) is wrapped along the exterior surface (1200). The marine cable device (1) in accordance with this embodiment comprises a further optical medium (225) in the form of a UV transparent silicone layer within which the first optical medium (220) in the form of a UV transparent fiber is embedded. Further in this embodiment the marine cable device (1) comprises a reflective layer (230) in between the optical medium (220) and the exterior surface (1200).

Figure 2:
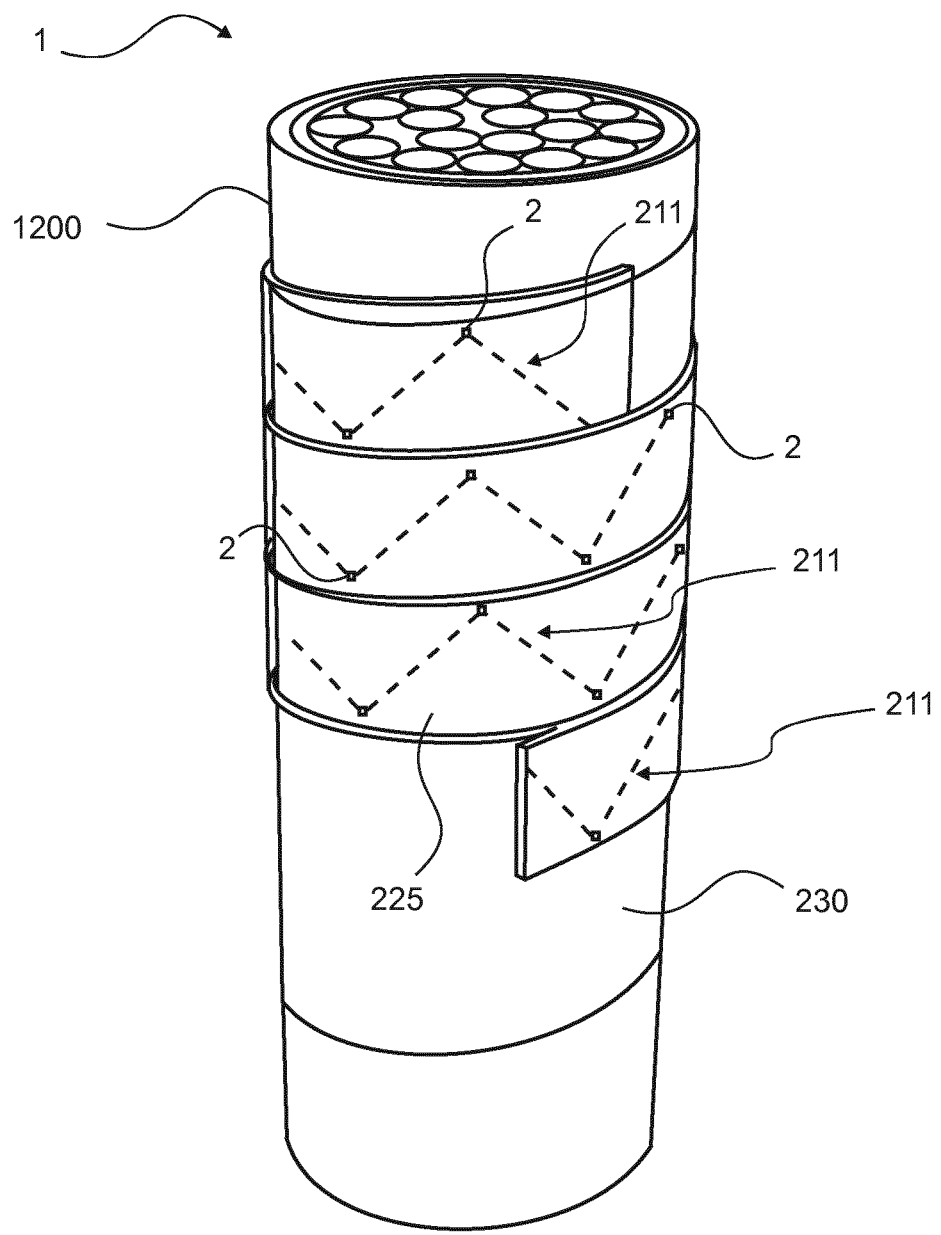
FIG. 2 is a schematic representation of another embodiment of the marine cable device.

FIG. 2 shows an alternative embodiment comprising an array of light sources (2) in the form of light-emitting diodes (LEDs). The optical medium (225) is a UV transparent silicone layer within which the LED light sources (2) are embedded. In this particular embodiment the optical medium (225) is in the form of a long narrow tape and the light sources (2) are positioned alternatingly on the top and the bottom sides of the said tape so as to provide light along the gull length of the optical medium (225) with optimal number of light sources (2). Further in this embodiment also the marine cable device (1) comprises a reflective layer (230) in between the optical medium (220) and the exterior surface (1200).

Figure 3:
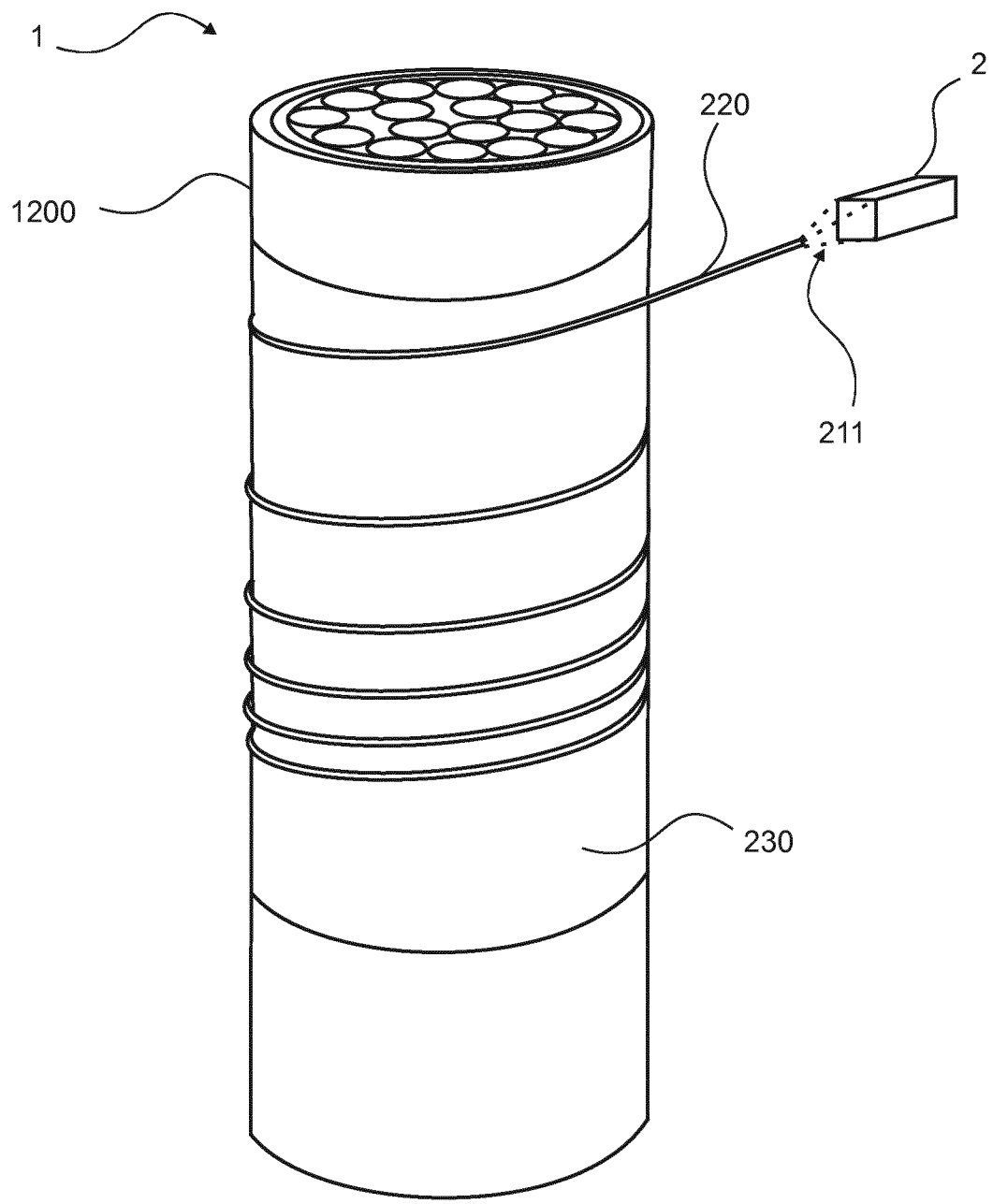
FIG. 3 is a schematic representation of an embodiment of the marine cable device wherein the optical medium is wrapped along the exterior surface with a variable pitch

FIG. 3 shows a further embodiment of the marine cable device (1) wherein the optical medium (220) is wrapped with variable pitch along at least part of the length of the marine cable device (1), arranged such that the pitch angle is smaller in the areas with more fouling risk.

Figure 4:
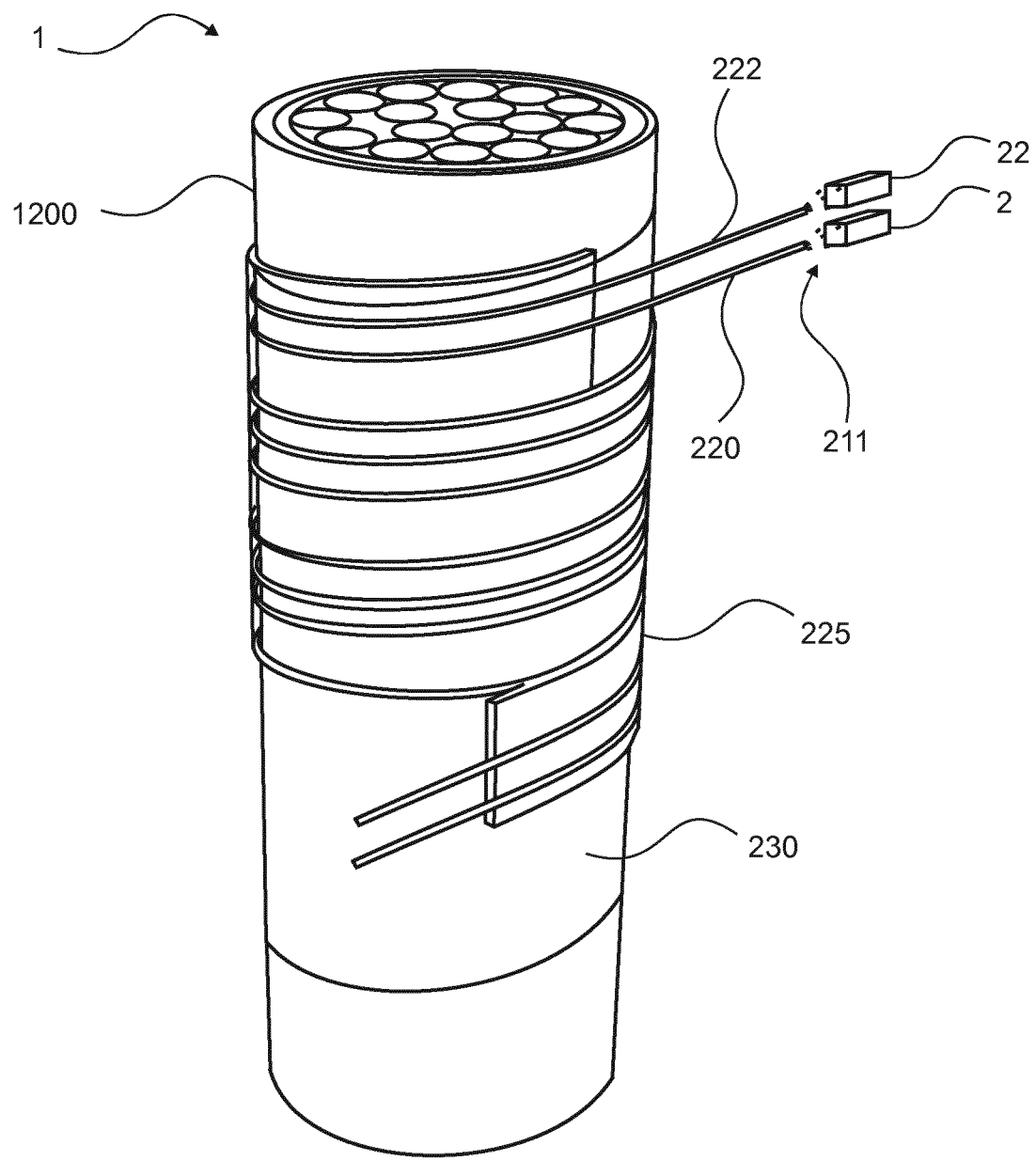
FIG. 4 is a schematic representation of an embodiment of the marine cable device wherein multiple optical mediums in the form of a fiber are used.

FIG. 4 shows an alternative embodiment of the marine cable device (1) comprising more than one optical medium (220, 222) in the form of a fiber along at least part of the length of the marine cable device (1). In this embodiment the optical mediums (220, 222) have different refractive indices and/or wavelengths.

Figure 5:
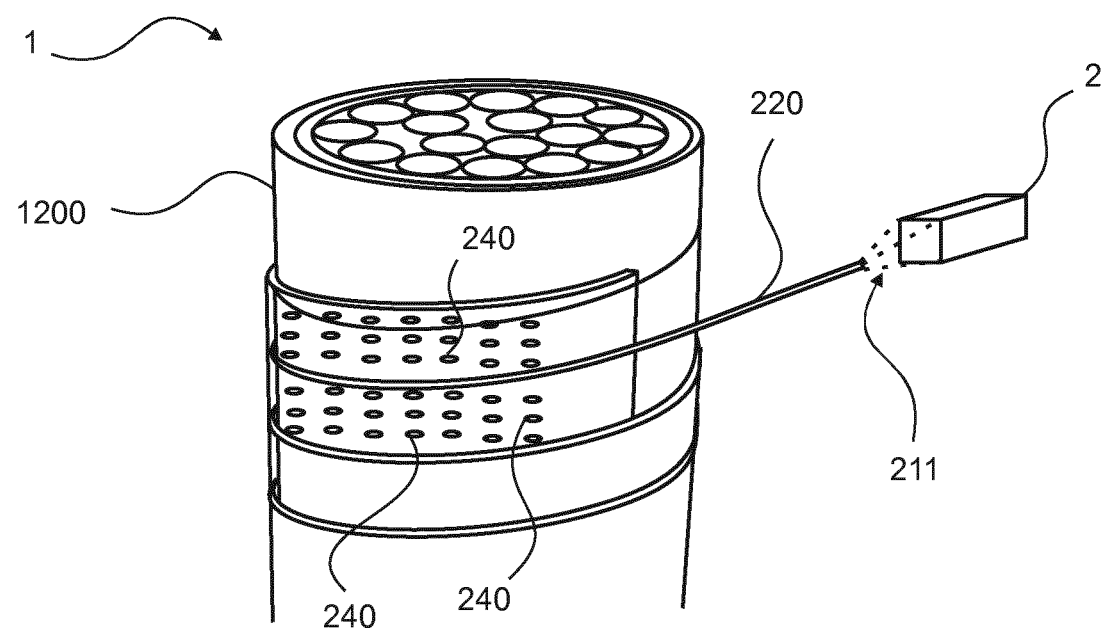
FIG. 5 is a schematic representation of an embodiment of the marine cable device comprising spacers.

FIG. 5 shows an alternative embodiment of the marine cable device (1) comprising more than one spacer (240) in between the reflective layer (230) and the exterior surface (1200). Multiple spacers (240) are arranged in an organized manner so as to provide a uniform layer of air or water in between the reflective layer (230) and the exterior surface (1200) and hence less of the anti-fouling light (211) is absorbed and accordingly more is provided on the areas with fouling.

Elements and aspects discussed for or in relation with a particular embodiment may be suitably combined with elements and aspects of other embodiments, unless explicitly stated otherwise. The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof. As fouling may also happen in rivers or lakes or any other area where the cooling apparatus is in contact with water, the invention is generally applicable to cooling by means of water.

The invention claimed is:

1. A marine cable device arranged to reduce biofouling along its exterior surface, comprising:
    at least one light source, wherein the light source is arranged to generate an anti-fouling light; and
    at least one optical medium, the optical medium comprising at least one emission surface wrapped along the exterior surface,
        wherein the wrapping has a variable pitch along at least part of the length of the marine cable device,
        wherein the at least one optical medium is arranged to receive at least part of the anti-fouling light,
        wherein the at least one optical medium is arranged to provide, through the emission surface, the at least part of the anti-fouling light on at least part of the exterior surface.
2. The marine cable device according to claim 1, wherein the anti-fouling light comprises at least one of a UV-A and a UV-C light.
3. The marine cable device according to claim 1,
    wherein the light source is a laser,
    wherein the at least one optical medium is in the form of a UV transparent fiber.
4. The marine cable device according to claim 1 wherein multiple emission surfaces are arranged to provide a uniform out-coupling of the anti-fouling light.
5. The marine cable device according to claim 1 wherein the at least one optical medium comprises at least one of a fiber and a tape.
6. The marine cable device according to claim 5,
    wherein the at least one optical medium is at least two optical mediums,
    wherein the at least two different optical mediums have different refractive indices.
7. The marine cable device according to claim 1 wherein the as least one light source comprises an array of light sources in the form of light-emitting diodes.
8. The marine cable device according to claim 1,
    wherein the at least one light source is embedded in the at least one optical medium,
    wherein the at least one optical medium is a UV transparent silicone layer.
9. The marine cable device as claimed in claim 1, comprising a reflective layer positioned between the at least one optical medium and the exterior surface.
10. The marine cable device according to claim 9, comprising at least one spacer between the reflective layer and the exterior surface.
11. The marine cable device according to claim 1 wherein the marine cable device is configured to transport at least one of data, electricity, water, gas or oil.
12. The marine cable device according to claim 1 wherein the marine cable device is configured to contact at least one of a vessel, a stationary marine structure, an offshore structure or a seismic surveying structure.
13. The marine cable of claim 1,
    wherein the optical medium is wrapped with a variable pitch angle along at least part of the length of the marine cable device,
    wherein the pitch angle of the optical medium is smaller in areas with more fouling risk.
14. The marine cable of claim 5, wherein the at least one light source provides the anti-fouling light at different wavelengths to corresponding ones of the at least one optical medium.
15. The marine cable according to claim 1, wherein the marine cable device is configured to carry, along the exterior surface, at least one of a sensor, an optical equipment or an electrical equipment.

* * * * *